US008398408B1

(12) United States Patent
Hansen et al.

(10) Patent No.: US 8,398,408 B1
(45) Date of Patent: Mar. 19, 2013

(54) CHARGING STATION FOR CORDLESS ULTRASOUND CART

(75) Inventors: Joshua M. Hansen, Everett, WA (US); Daniel Davidson, Seattle, WA (US); Richard A. Fine, Mercer Island, WA (US)

(73) Assignee: SonoSite, Inc., Bothell, WA (US)

( * ) Notice: Subject to any disclaimer, the term of this patent is extended or adjusted under 35 U.S.C. 154(b) by 538 days.

(21) Appl. No.: 12/616,642

(22) Filed: Nov. 11, 2009

Related U.S. Application Data

(63) Continuation-in-part of application No. 12/392,869, filed on Feb. 25, 2009, now abandoned.

(51) Int. Cl.
*H01R 33/00* (2006.01)

(52) U.S. Cl. ............... 439/34; 320/109; 361/679.41

(58) Field of Classification Search .................. None
See application file for complete search history.

(56) References Cited

U.S. PATENT DOCUMENTS

| | | | |
|---|---|---|---|
| 4,009,429 A | 2/1977 | Mullersman | |
| 4,285,391 A | 8/1981 | Bourner | |
| 5,252,078 A * | 10/1993 | Langenbahn | 439/34 |
| 5,498,948 A | 3/1996 | Bruni et al. | |
| 5,603,323 A | 2/1997 | Pflugrath et al. | |
| 5,617,003 A | 4/1997 | Odachi et al. | |
| 5,640,960 A | 6/1997 | Jones et al. | |
| 5,687,717 A | 11/1997 | Halpern et al. | |
| 5,715,823 A | 2/1998 | Wood et al. | |
| 5,729,587 A | 3/1998 | Betz | |
| 5,795,297 A | 8/1998 | Daigle | |
| 5,814,968 A | 9/1998 | Lovegreen et al. | |
| 5,821,731 A | 10/1998 | Kuki et al. | |
| 5,850,135 A * | 12/1998 | Kuki et al. | 320/108 |
| 5,851,186 A | 12/1998 | Wood et al. | |
| 5,888,087 A | 3/1999 | Hanson et al. | |
| 5,891,035 A | 4/1999 | Wood et al. | |
| 5,892,299 A | 4/1999 | Siewert et al. | |
| 5,897,498 A | 4/1999 | Canfield, II et al. | |
| 5,938,607 A | 8/1999 | Jago et al. | |
| 5,963,014 A | 10/1999 | Chen | |
| 6,031,356 A | 2/2000 | Harada et al. | |
| 6,117,085 A | 9/2000 | Picatti et al. | |
| 6,142,940 A | 11/2000 | Lathbury et al. | |
| 6,182,663 B1 * | 2/2001 | Madden | 128/845 |
| 6,241,673 B1 | 6/2001 | Williams | |
| 6,312,381 B1 | 11/2001 | Knells | |
| 6,364,839 B1 | 4/2002 | Little et al. | |
| 6,371,230 B1 | 4/2002 | Ciarla et al. | |
| 6,424,120 B1 | 7/2002 | Chen | |
| 6,435,109 B1 | 8/2002 | Dell et al. | |
| 6,436,039 B1 | 8/2002 | Lannutti et al. | |
| 6,443,543 B1 | 9/2002 | Chiang | |

(Continued)

*Primary Examiner* — Michael Zarroli
(74) *Attorney, Agent, or Firm* — Perkins Coie LLP

(57) ABSTRACT

The present invention is directed to a system and method which establishes physically fixed charger stations that work in conjunction with a medical cart, such as an ultrasound cart. The medial cart contains a power supply, such as a large battery, with the capacity to keep the system going for a full day's use. Each docking station provides a fixed location for one or more carts and allows each cart to plug directly into a source of premises power. The docking stations allow the plugged-in cart to recharge while the cart is not in use. In one embodiment, a large Class C battery capable of powering not only the medical device but its associated peripherals as well. Thus, when the cart is removed from the docking station and taken to a patient's location, the equipment on the cart can be operated without the need for plugging the cart into a wall outlet thereby eliminating the need for a long power cord. The fixed locations of the docking station also eliminates the need for hunting "misplaced" carts.

12 Claims, 11 Drawing Sheets

U.S. PATENT DOCUMENTS

| | | |
|---|---|---|
| 6,468,213 B1 | 10/2002 | Knell et al. |
| 6,471,651 B1 | 10/2002 | Hwang et al. |
| 6,488,625 B1 | 12/2002 | Randall et al. |
| 6,493,217 B1 | 12/2002 | Jenkins, Jr. |
| 6,493,220 B1 | 12/2002 | Clark et al. |
| 6,497,664 B1 | 12/2002 | Randall et al. |
| 6,508,763 B1 | 1/2003 | Urbano et al. |
| 6,517,491 B1 | 2/2003 | Thiele et al. |
| 6,524,244 B1 | 2/2003 | Knell et al. |
| 6,525,509 B1 | 2/2003 | Petersson et al. |
| 6,525,510 B1 | 2/2003 | Ayano et al. |
| 6,542,846 B1 | 4/2003 | Miller et al. |
| 6,561,979 B1 | 5/2003 | Wood et al. |
| 6,586,908 B2 * | 7/2003 | Petersson et al. .............. 320/107 |
| 6,592,521 B1 | 7/2003 | Urbano et al. |
| 6,595,921 B1 | 7/2003 | Urbano et al. |
| 6,629,928 B1 | 10/2003 | Dolan et al. |
| 6,716,167 B1 | 4/2004 | Henderson et al. |
| 6,721,178 B1 | 4/2004 | Clark et al. |
| 6,817,879 B2 * | 11/2004 | Mulvenna et al. ............ 439/310 |
| 6,852,081 B2 | 2/2005 | Sumanaweera et al. |
| 6,980,419 B2 | 12/2005 | Smith et al. |
| 7,009,840 B2 | 3/2006 | Clark et al. |
| 7,013,163 B2 | 3/2006 | Jaggers et al. |
| 7,037,264 B2 | 5/2006 | Poland |
| 7,037,267 B1 | 5/2006 | Lipson et al. |
| 7,141,020 B2 | 11/2006 | Poland et al. |
| 7,188,621 B2 | 3/2007 | DeVries et al. |
| 7,236,087 B2 | 6/2007 | Vasquez et al. |
| 7,332,890 B2 | 2/2008 | Cohen et al. |
| 7,560,071 B2 * | 7/2009 | Nichols et al. .................. 422/63 |
| 7,591,786 B2 | 9/2009 | Holmberg et al. |
| 7,594,668 B2 | 9/2009 | Arceta et al. |
| 7,612,999 B2 | 11/2009 | Clark et al. |
| 7,621,544 B2 | 11/2009 | Rossini |
| 7,679,522 B2 | 3/2010 | Carpenter |
| 7,817,415 B2 * | 10/2010 | Chuang ................... 361/679.43 |
| 7,849,250 B2 | 12/2010 | Diener et al. |
| 8,098,044 B2 * | 1/2012 | Taguchi ....................... 320/109 |
| 2001/0055978 A1 | 12/2001 | Herrod et al. |
| 2002/0016545 A1 | 2/2002 | Quistgaard et al. |
| 2002/0070516 A1 | 6/2002 | Haas et al. |
| 2002/0103007 A1 | 8/2002 | Jaggers et al. |
| 2002/0143256 A1 | 10/2002 | Wing et al. |
| 2004/0004460 A1 | 1/2004 | Fitch et al. |
| 2004/0150963 A1 | 8/2004 | Holmberg et al. |
| 2004/0152982 A1 | 8/2004 | Hwang et al. |
| 2004/0158154 A1 | 8/2004 | Hanafy et al. |
| 2006/0098864 A1 | 5/2006 | Ziel |
| 2007/0274693 A1 | 11/2007 | Farbarik |
| 2008/0316045 A1 | 12/2008 | Sriharto et al. |
| 2010/0228405 A1 * | 9/2010 | Morgal et al. ..................... 701/2 |

\* cited by examiner

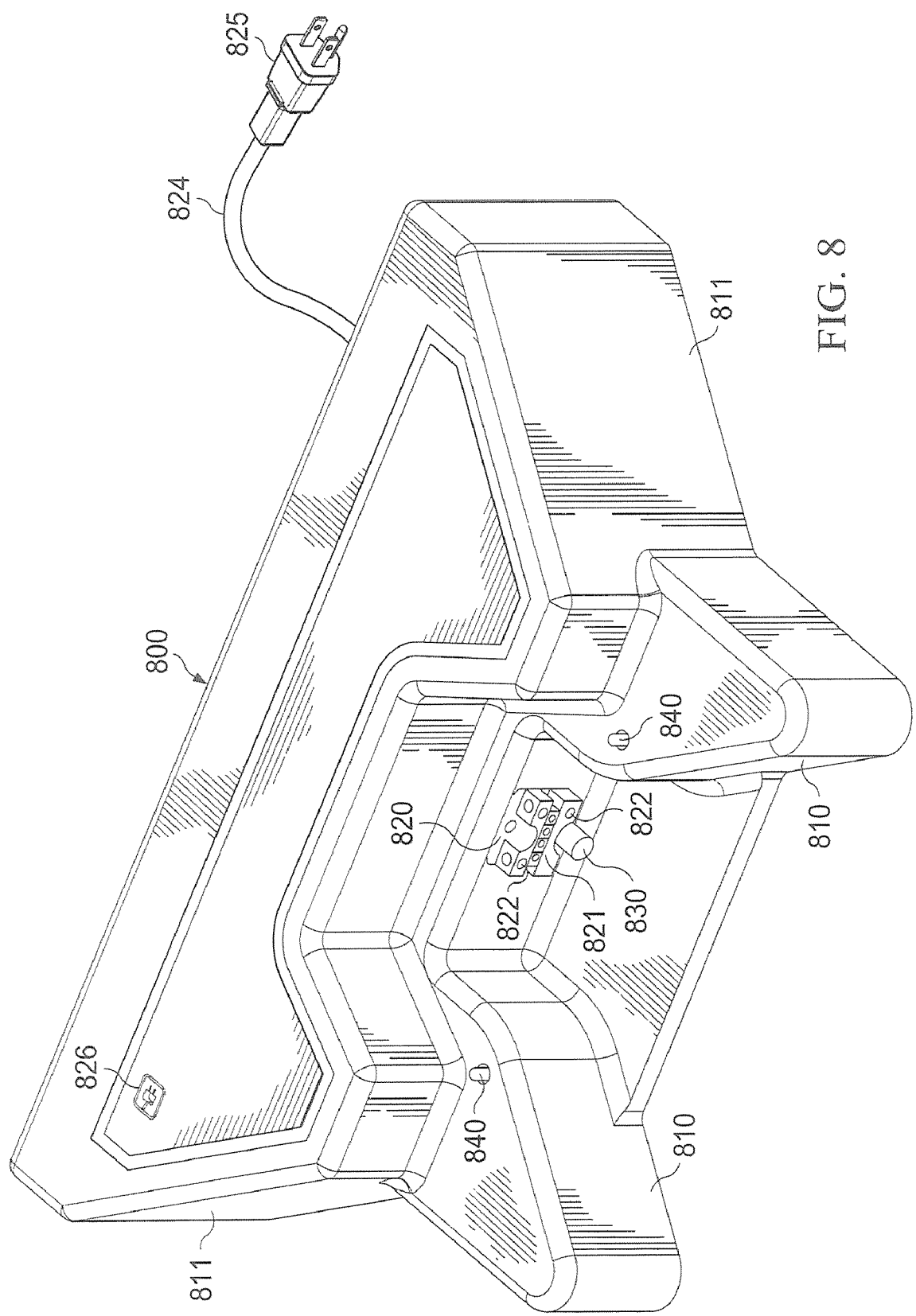

CHARGING STATION FOR CORDLESS ULTRASOUND CART

CROSS-REFERENCE TO RELATED APPLICATIONS

The present application is a continuation-in-part of co-pending, commonly assigned U.S. patent application Ser. No. 12/392,869 entitled "CHARGING STATION FOR CORDLESS ULTRASOUND CART," filed Feb. 25, 2009, and this application is related to U.S. patent application Ser. No. 11/590,010 filed Oct. 31, 2006, entitled "DOCKING STATION HAVING AUXILIARY POWER MANAGEMENT FOR USE WITH PORTABLE MEDICAL EQUIPMENT," the disclosures of which are hereby incorporated herein by reference.

TECHNICAL FIELD

This disclosure relates to battery charging systems and more particularly to systems and methods for maintaining the batteries within a portable medical device cart charger.

BACKGROUND OF THE INVENTION

It is now common practice in a variety of situations to use portable medical devices, such as ultrasound devices, for examination of patients at the location of the patient. Often this location is the patient's bed in a hospital room. The portable device can be brought to the patient for the examination and in such a situation, the portable device operates from batteries internal to the device. The portable device, in one embodiment, resides on a movable cart and plugs into the cart for recharging. The cart, in turn, plugs into a premises power supply and operates to supply a source of power for both operating the portable device while the device is attached to the cart and for recharging the device's internal batteries. The cart also provides a source of power for peripheral equipment, such as printers, displays, etc. used with the medical device. Thus the cart requires a power cord long enough to plug into the premises source of power which is a wall outlet.

Several problems exist when the cart is moved to a patient's bedside. Some of these problems revolve around the fact that often there is a myriad of equipment plugged into the wall outlets in a patient's room and available outlets are scarce. Even when outlets are available, they typically are a large distance from where the cart is to be used thereby necessitating a long power cord attached to the cart. In addition to the problem of simply running this cord from the cart to the wall outlet, there is the problem of containing the cord when the cart is being moved from location to location. Long power cords, as anyone who has used an electric vacuum sweeper well knows, have a disconcerting affinity for becoming tangled, caught on furniture and getting underfoot. In general, power cords on devices, particularly long power cords used in cramped conditions, are a general nuisance and worse, often unsafe.

In the medical setting discussed above, when the carts are not in actual use with a patient they are moved off to the side and often the operator forgets to plug in the cart. However, even if the operator remembers to plug in the cart, there is not always an available power outlet in close proximity to the present location of the cart. Thus, the cart operator then must hunt down a suitable location to "park" the cart. Often this suitable location is based on physical space and not on power availability. This then results in the failure to recharge the portable medical equipment residing on the cart.

Another problem is that the carts tend to be left available area randomly (usually in a location near where they were last used, with or without being plugged into a power outlet) and thus when the next user desires the use of the cart a search is often required to locate an available cart. This then wastes valuable time of doctors and practitioners either while they look for the cart or while a procedure they wish to be perform is delayed while someone else hunts down the cart.

BRIEF SUMMARY OF THE INVENTION

The present invention is directed to systems and methods which establish physically fixed or semi-fixed charger stations that work in conjunction with a mobile cart, such as an ultrasound cart. The cart may comprise a power supply, such as a large battery, with the capacity to keep one or more devices of the system thereof operating, such as to provide operation for a full day's use. Similarly, devices on or of the cart may additionally or alternatively comprise such a power supply for facilitating their use. Docking stations of embodiments herein provide a fixed or semi-fixed location for one or more carts and allow each cart to plug directly into a source of premises power.

Docking stations and carts of embodiments of the invention are correspondingly adapted to facilitate interfacing (also referred to herein as "docking") a cart with a docking station wherein electrical and/or other connections are completed without further human intervention. That is docking stations and carts of embodiments comprise interface surfaces adapted to guide the relative movement between the docking components such that the desired connections are completed when docked.

Docking a cart with a docking station provides power and/or other services (e.g., network communication link, data upload, data download, etc.) for operation of the cart and devices thereof according to embodiments. Additionally or alternatively, docking a cart with a docking station allows the plugged-in cart to recharge while the cart is not in use according to embodiments. For example, in one embodiment, a large Class C battery capable of powering not only a medical device component but also its associated peripheral devices (e.g., printer, external monitor, etc.) may be present on the cart and provided recharging when the cart is docked with a docking station. Thus, when the cart is removed from the docking station and taken to a patient's location, the equipment on the cart can be operated without the need for plugging the cart into a wall outlet thereby eliminating the need for a long power cord.

Embodiments of carts operable with respect to docking stations herein are adapted to accommodate connection of the cart and/or devices thereof to a source of premises power without being docked with a docking station. For example, an auxiliary power connector is provided according to embodiments to facilitate connection to premises power when in an area having no docking stations, in an emergency situation when battery power is depleted, when a docking station is not available, etc. Embodiments implement a power switching mechanism to facilitate switching between such an auxiliary power connector and a docking station connector. For example, an automatic power switching mechanism is utilized to provide selection of a docking station connector as a source of premises power when a cart is docked with a docking station of embodiments herein. Such power switching mechanisms may additionally provide for isolation of a non-selected power connector, such as to provide a safety interrupt preventing an unused such power connector from becoming energized by energy provided by a power connector which is connected to premises power.

Docking stations of embodiments herein may be disposed in various locations. For example, fixed locations may be selected, such as in a hospital hallway, nurses' station, surgical suite core, etc., for one or more docking station to eliminate hunting for "misplaced" carts, available/suitable power outlets, etc.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which:

FIG. 8 shows an embodiment of a docking station;

DETAILED DESCRIPTION OF THE INVENTION

Figure 1:
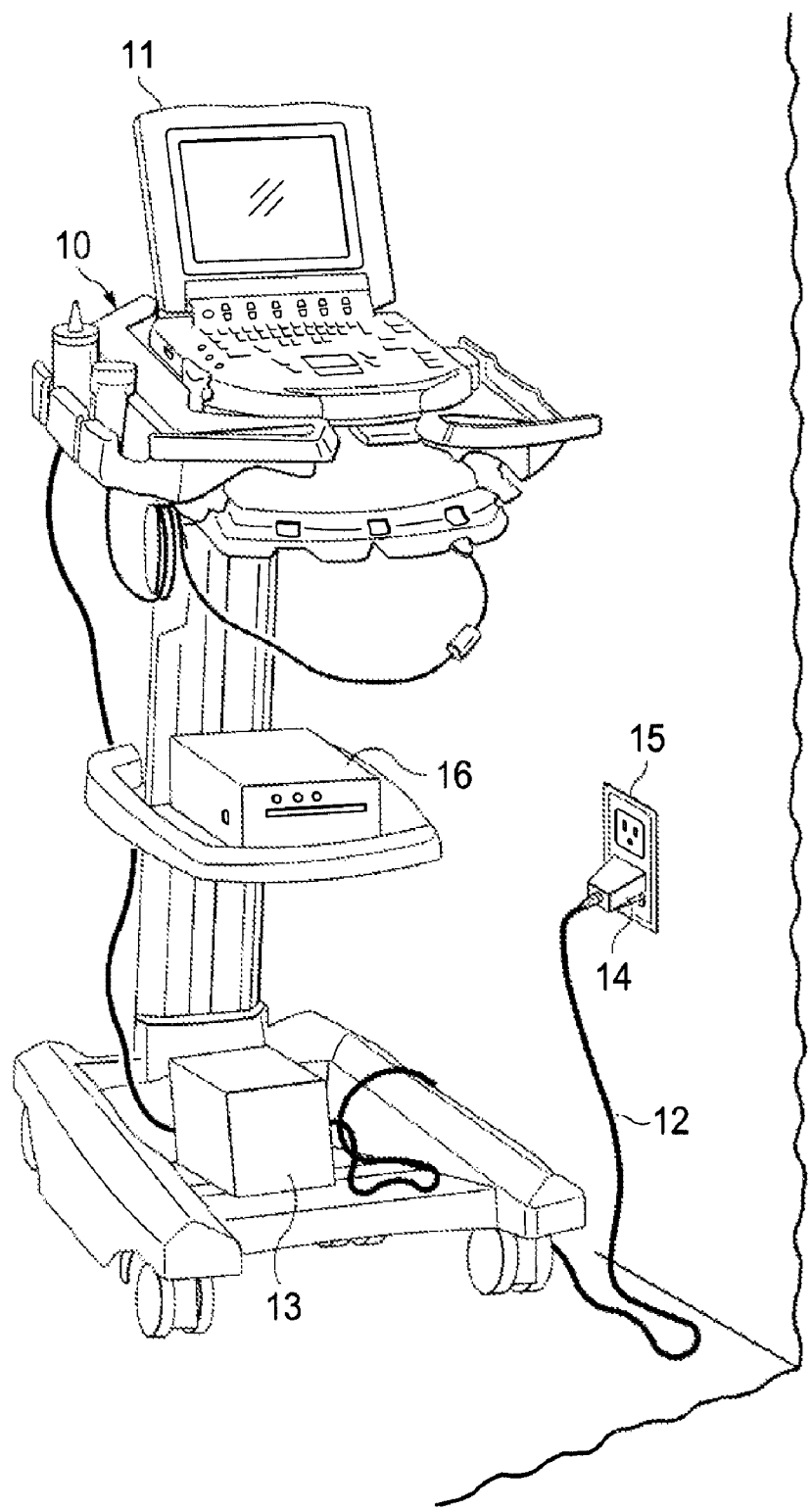
FIG. 1 shows a typical prior art medical cart of the type used for sonography equipment.

FIG. 1 shows a typical prior art medical cart 10 of the type used for sonography equipment, such as device 11. The ultrasound system could have an internal battery (not shown). Note that in this case the ultrasound cart does not have a battery but it does have power outlet 13 connected to long cord 12. The cord has plug end 14 which is adapted to plug into a wall outlet, such as wall outlet 15 to provide power to the system. Auxiliary equipment 16 is plugged into outlet box 13. This could be, for example, a printer, a video recorder, a VCR or any other type of equipment, all of which receive power from the cart, via the premises power outlet. As discussed above, when the power plug is removed from the wall outlet none of the auxiliary equipment can operate unless it has internal battery power.

In operation, when it is desired to move the cart to a patient location the cord is unplugged and wrapped around the cart, or onto a reel, or most often, held in the hand of the cart operator. When the cart gets to the proper location, the operator locates a convenient (often not so convenient) outlet and plugs the cart into the premises power. If power is not available, only those pieces of equipment on the cart that have internal batteries can function until their batteries run down. In any event, the cart must be plugged in for the peripherals to work since in almost all cases they do not have internal power.

Figure 2:
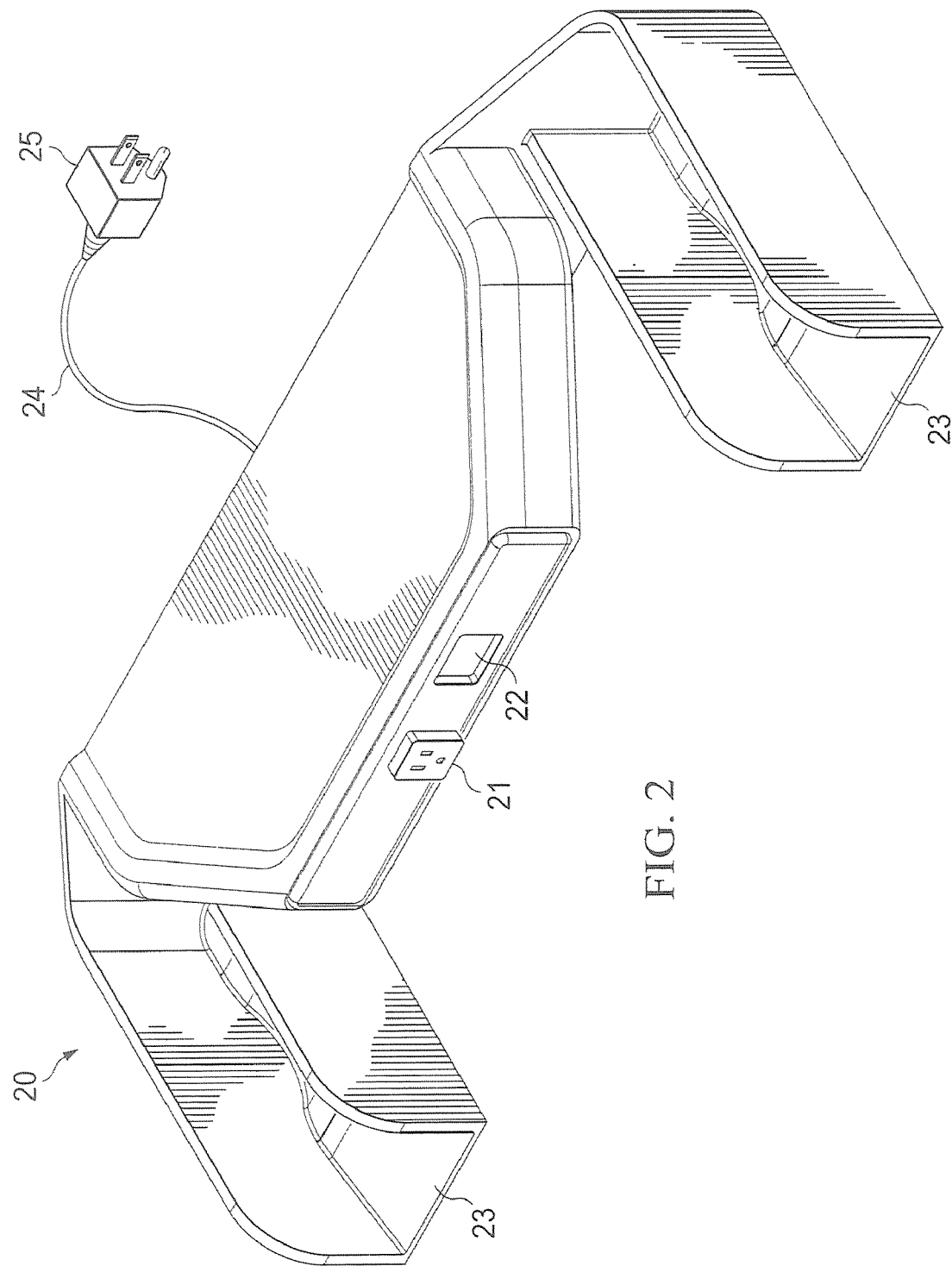
FIG. 2 shows one embodiment of a cart docking station.

FIG. 2 shows one embodiment 20 of a cart docking station. The docking station has at least one power connector 21 for mating with a mobile cart (shown in FIG. 3). Other connectors, such as connector 22, can be used to connect other connections, such as network connections, to the cart for downloading or uploading data from and to the cart. Openings 23 in this embodiment are designed to accept the wheeled legs of the cart when the cart is mated (docked) with the docking station. The docking station can be hard wired into the premises wiring (not shown) or it can be connected to a wall outlet via cord 24 and plug 25. If desired, a plurality of docking stations 20 can be positioned at a single location.

Note that while not shown, the docking station can have built into it one or more power shaping controls, such as UPS or power converters, so that the carts can have equipment that runs at a different voltage or frequency than the premises power. This, then would reduce the cost of each individual medical service cart. The docking station is designed to be permanently, or at least semi-permanently, positioned at a particular physical location. This positioning can be. for example, by making the docking station not easily movable or positioning the clocking station within a defined space, or even by fastening the docking station to the premises.

In operation, when it is desired to dock a medical service cart at the docking station, the operator simply lines up the cart with the docking station and then pushes the cart by its handle into the dock. The power and (if available) the network connections are then made from the docking station to the cart without further human intervention. Cups 23, in the embodiment shown, serve as an aid to positioning the cart with respect to the docking station. The cups are designed to mate with wheels of the cart. Other positioning aids can be employed including aids not physically attached to the docking station.

Figure 3:
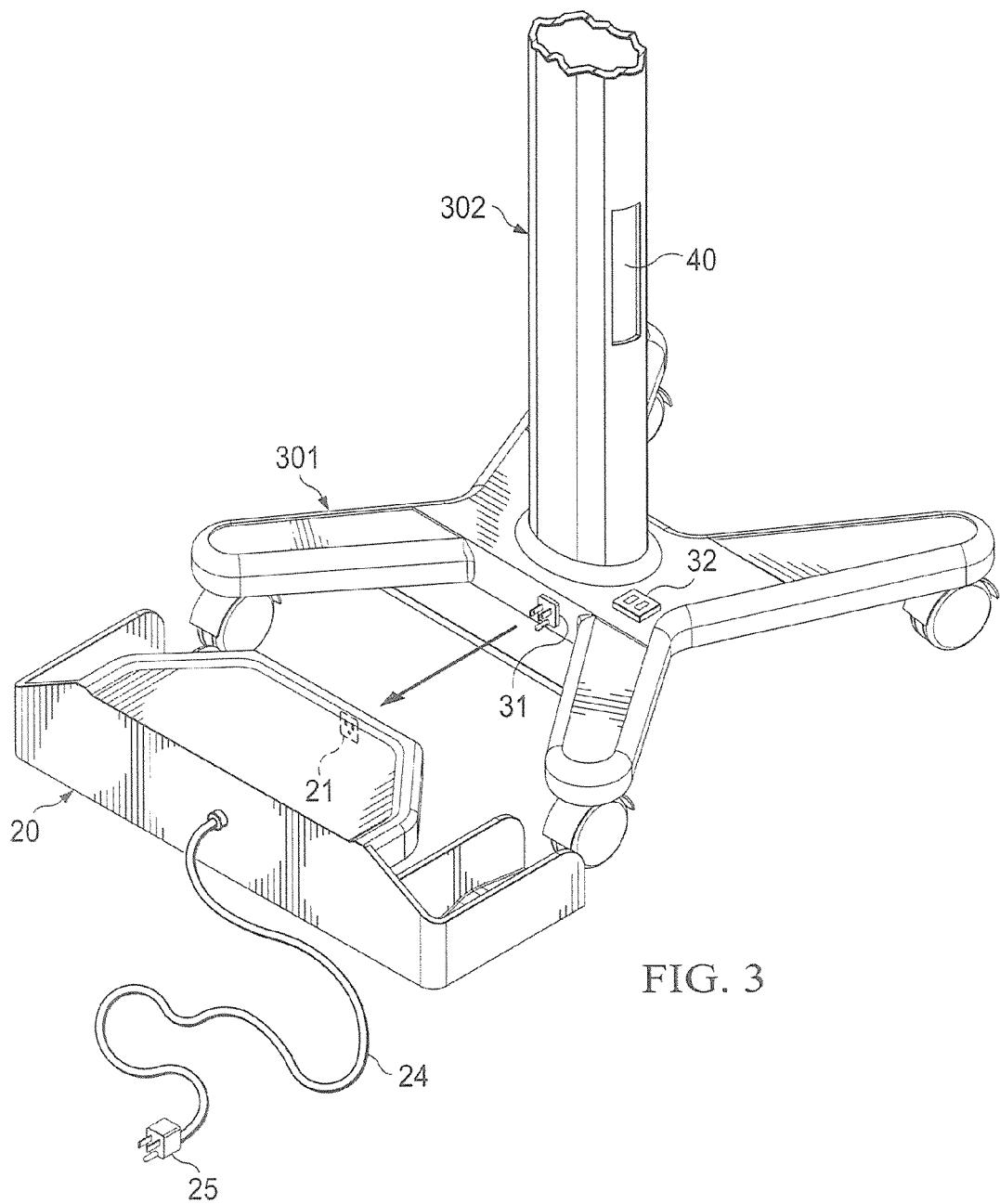
FIG. 3 shows one embodiment of a cart base about to be docked into a docking station.

FIG. 3 shows one embodiment of base 301 of a cart (only cart strut 302 is shown) about to be docked into docking station 20. The male end of plug 31 is shown about to be mated with connector 21 of docking station 20. The plug connector is in a fixed position on said cart so that it can mate with a mating connector located on a dock without human intervention. Note that while the male connector is shown on the cart and the female on the dock, the reverse could be used, if desired. If networking connections are included, they also would be in a fixed position (not shown in FIG. 3) about to be mated as the cart comes into docking position with respect to the docking station. The exact shape of the docking station is not critical, providing the attendant can easily move the cart into position with respect to the docking station in order for power and, if applicable, networking or other electrical connections, to be completed. Note that the fixed position of the various connectors on the cart are fixed relative to a docking station and this fixed position would be at the same location on all carts that mate with the docking station, or with similar docking stations. If desired, near-field electrical charging could be accomplished between the docking station and the cart and near-field electronic communications can also occur if hard-wired connections are not desirable. Once the cart is in docked relationship with the docking station, power is supplied to charge the on-cart batteries which, in this embodiment, are shown in device 40, FIG. 4.

Figure 4:
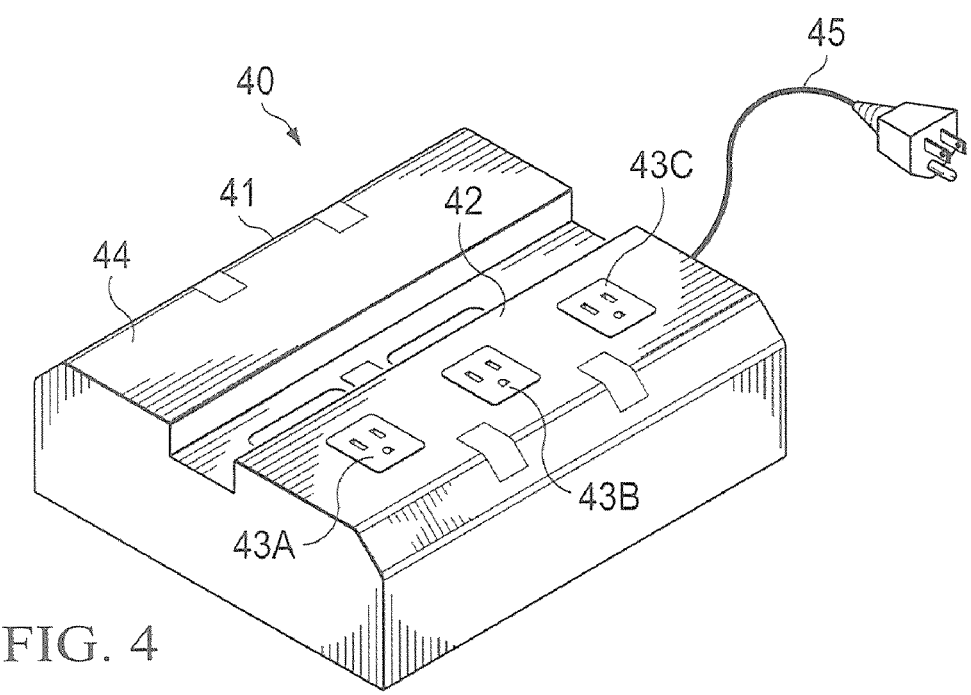
FIG. 4 shows one embodiment of an on-cart battery system.

FIG. 4 shows one embodiment of on-cart battery system 40 having at least one rechargeable battery section 44 and a power strip section 42. The power strip is shown having thereon a plurality of power outlets 43A, 43B and 43C, wherein equipment on the cart can plug into outlets 43A-43C or their equivalents. In the embodiment shown in FIG. 4, battery system 40 is connectable to a source of external power via cord 45. As discussed above, cord 45 would plug into a power outlet (such as power outlet 32, FIG. 3) on the base of the cart so that device 40 can obtain power for internal charging, etc. when the cart is docked to the docking station. As noted above, the on-cart battery system can be hard wired to the cart if desired and outlets 43A-43C can, if desired, be positioned at various locations on the cart convenient to the device(s) that they serve. In one embodiment, the rechargeable battery would serve to power the sonography equipment, a printer and a recorder when the cart is undocked from the docking station. In addition to or in the alternative to on-cart battery system 40, one or more devices on the cart may comprise batteries which are provided energy via a docking station.

Typically, the power requirement for a cart would be approximately 150 w at 110v. Such power requirement may be met by one or more on-cart battery systems, one or more battery internal to the devices, or combinations thereof. Any or all such batteries may be provided with recharging energy by docking stations of embodiments of the present invention. A battery charging and/or discharging hierarchy may be implemented, such as disclosed in the above referenced patent application entitled "Docking Station Having Auxiliary Power Management For Use With Portable Medical Equipment," to optimize device battery life.

In some embodiments where extensive use of the equipment is not necessary after the cart is disconnected from the docking station, cart batteries may not be desired. In such situations, in place of the battery and battery charging system a power supply can be used, Also if desired, voltages other than 110 can be supplied by the on-cart power supply and/or battery system. If desired, a built-in surge protector could be provided as could alternative energy sources, such as thermal or solar. Also, battery charging circuitry can be positioned on the docking system to charge one or more batteries on the cart.

Figure 5:
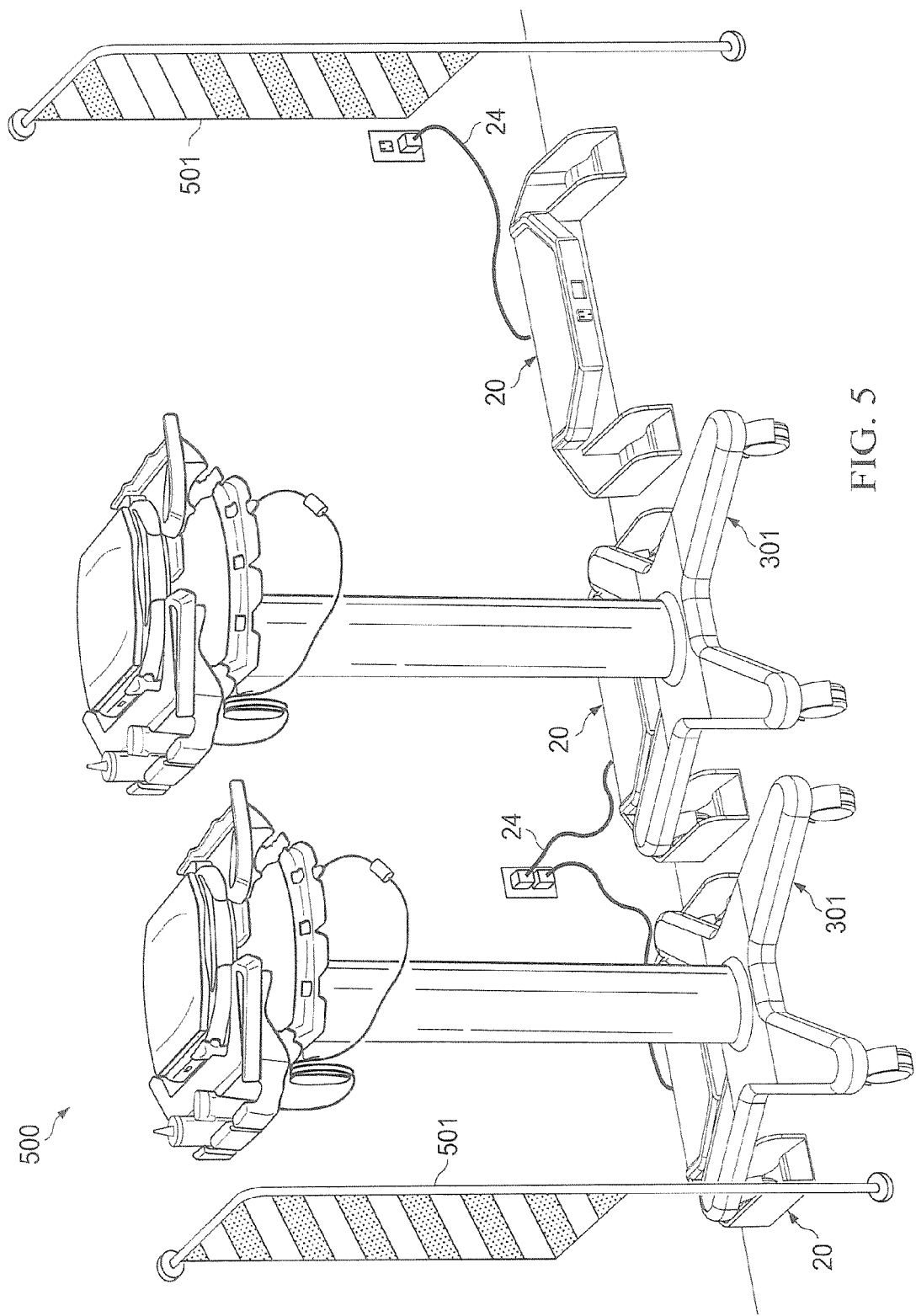
FIG. 5 shows one embodiment of multi-cart docking station.

FIG. 5 shows one embodiment of multi-cart docking station configuration having three individual docking stations 20 delineated by permanently affixed flags 501 on either end of the docking station system. Note that the individual docking stations can be connected to power sources individually as shown in FIG. 5 or they can be daisy-chained with each other, as shown in FIG. 6, and connected to the premises power source with a common power connection.

Figure 6:
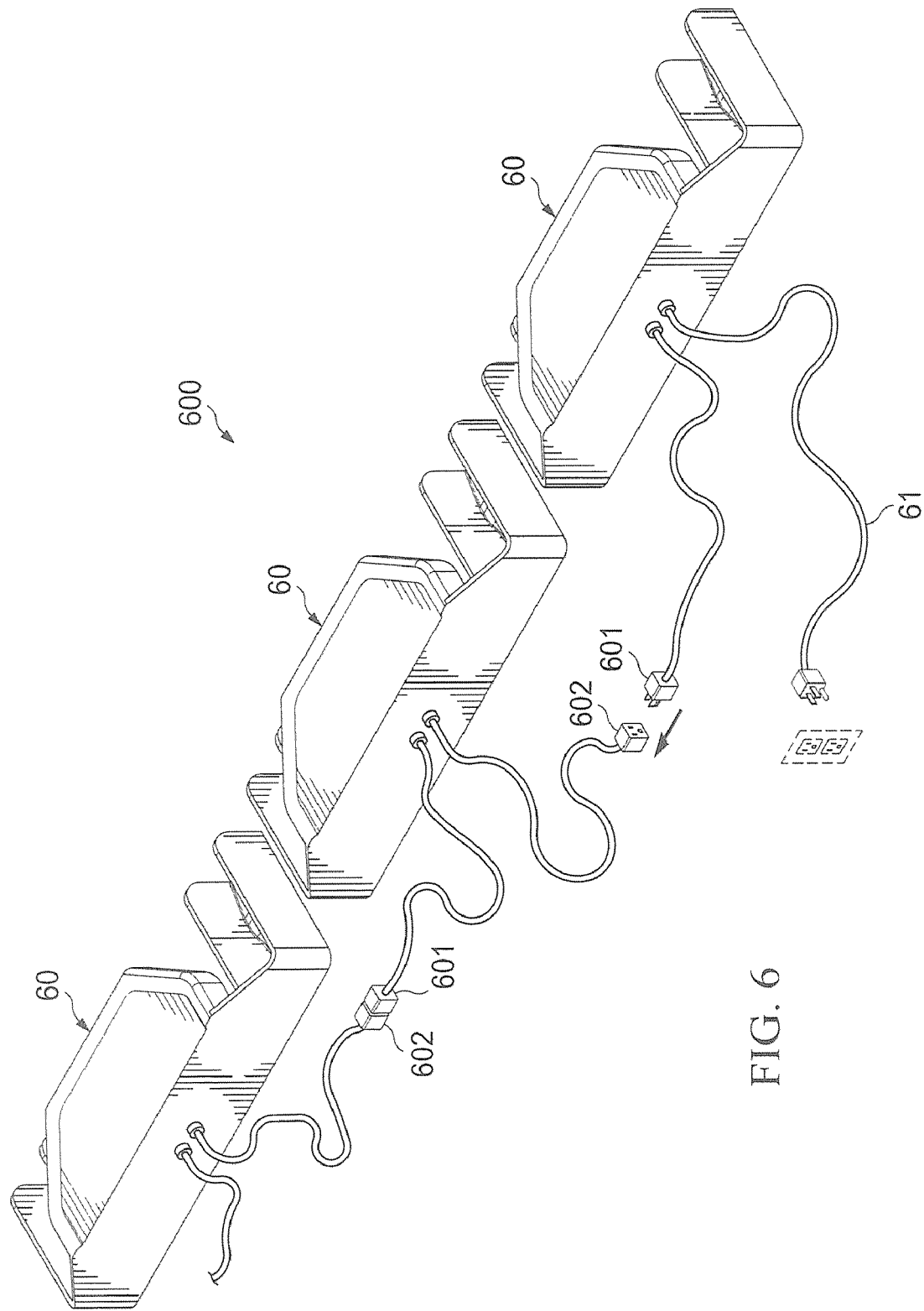
FIG. 6 shows one embodiment of a multiple docking system.

FIG. 6 shows one embodiment of a multiple docking station configuration in which individual docking stations 60 physically and electrically inter-connectable to form a multi-cart docking station system. One docking station could be wired to the premises, for example using connection 61. The interconnection shown in FIG. 6 is by use of external power cords 601 and 602 between the individual docking stations, but the clocking stations can be designed to mechanically fit together with the mechanical linkage including power distribution without the use of interconnecting external cords. Any number of individual docking stations can be connected provided only that the wiring and premises circuit breakers are sufficiently sized to carry the load occasioned by all docking stations having carts positioned therein and simultaneously charging their respective on-cart batteries. The power load requirement for an individual cart would be expected to be in the range of 150 w according to embodiments.

If desired, docking stations can be mounted permanently or semi-permanently in various rooms so that when a cart comes into a room the cart can mate with the docking station and obtain power and be able to communicate information from the sonographic equipment to permanently mounted displays in the room and to a central data collection/monitoring location. This would be especially useful in an operating theatre where big displays are mounted so that the doctors can see the display while they are operating. This would allow the ultrasound system to be plugged in away from the bed in a pre-assigned location but at the same time allow the sonographic equipment to work in conjunction with all the other medical devices being used in that operating theatre.

An operating theatre or a room or any other place could have several docking stations available at different locations so that the cart can be positioned as desired from time to time, even being relocated during a procedure without losing communications or power.

While the cart is in the docking station the network connections could provide updates to the software of the devices on the cart particularly when they are not being used, such as in the middle of the night. Also, information that had been recorded all day could then be sent to a premises system, or other system, for storage and or further processing and distribution.

Figure 7:
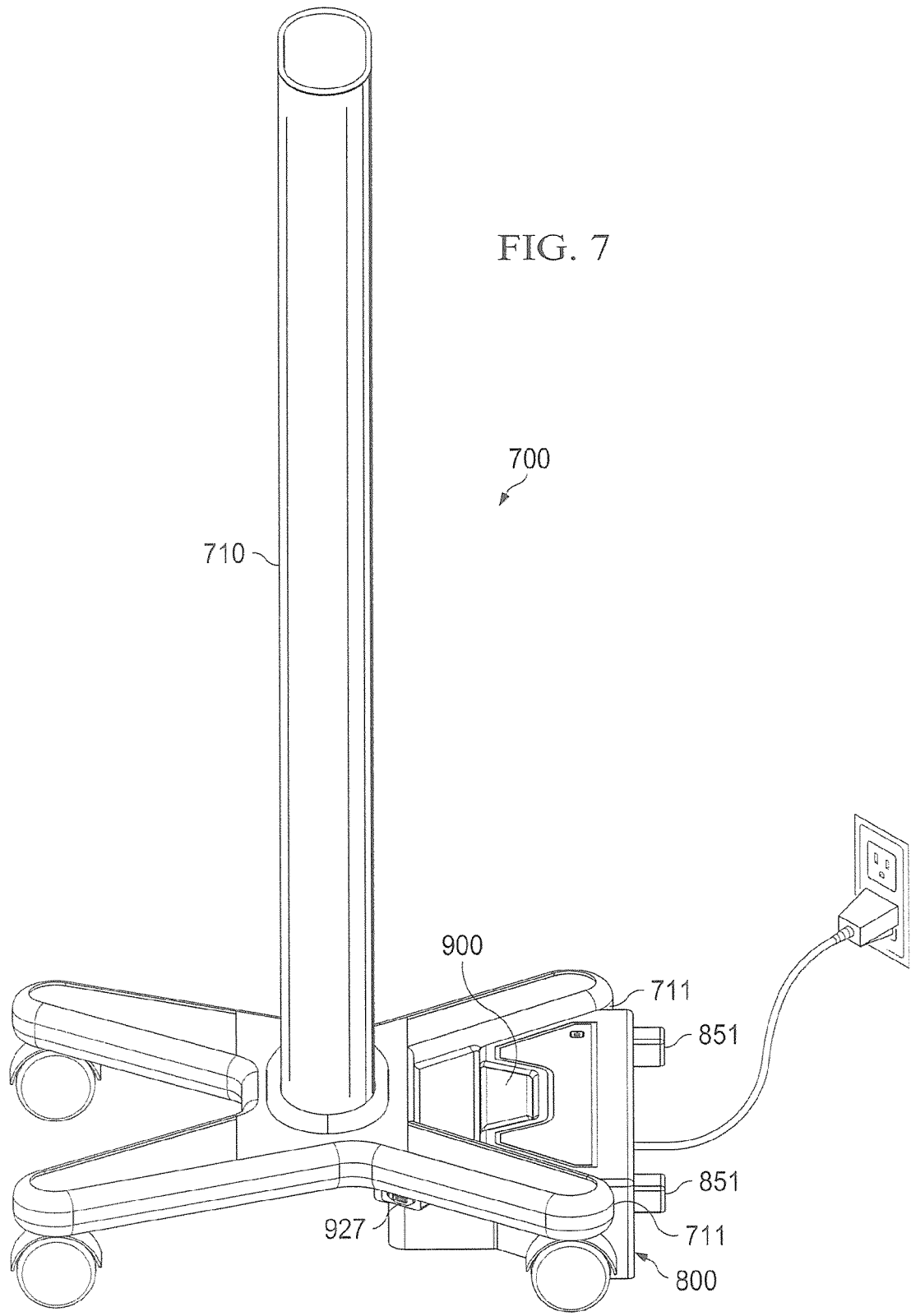
FIG. 7 shows an embodiment of a docking cart system.
Figure 9A:
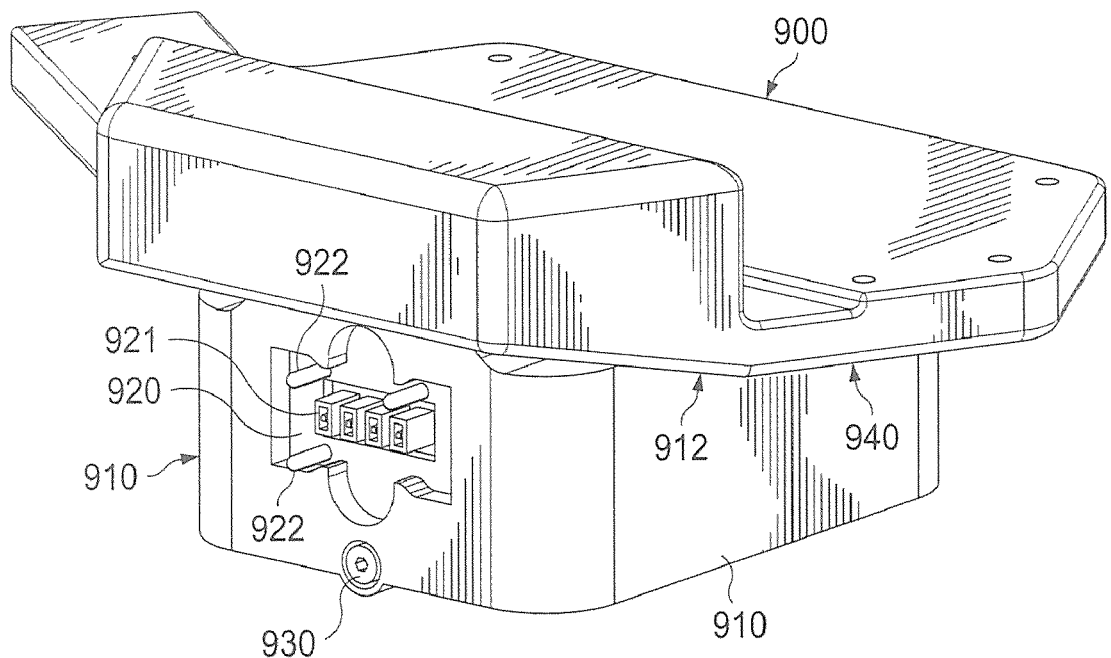
FIGS. 9A and 9B show an embodiment of a docking head.
Figure 9B:
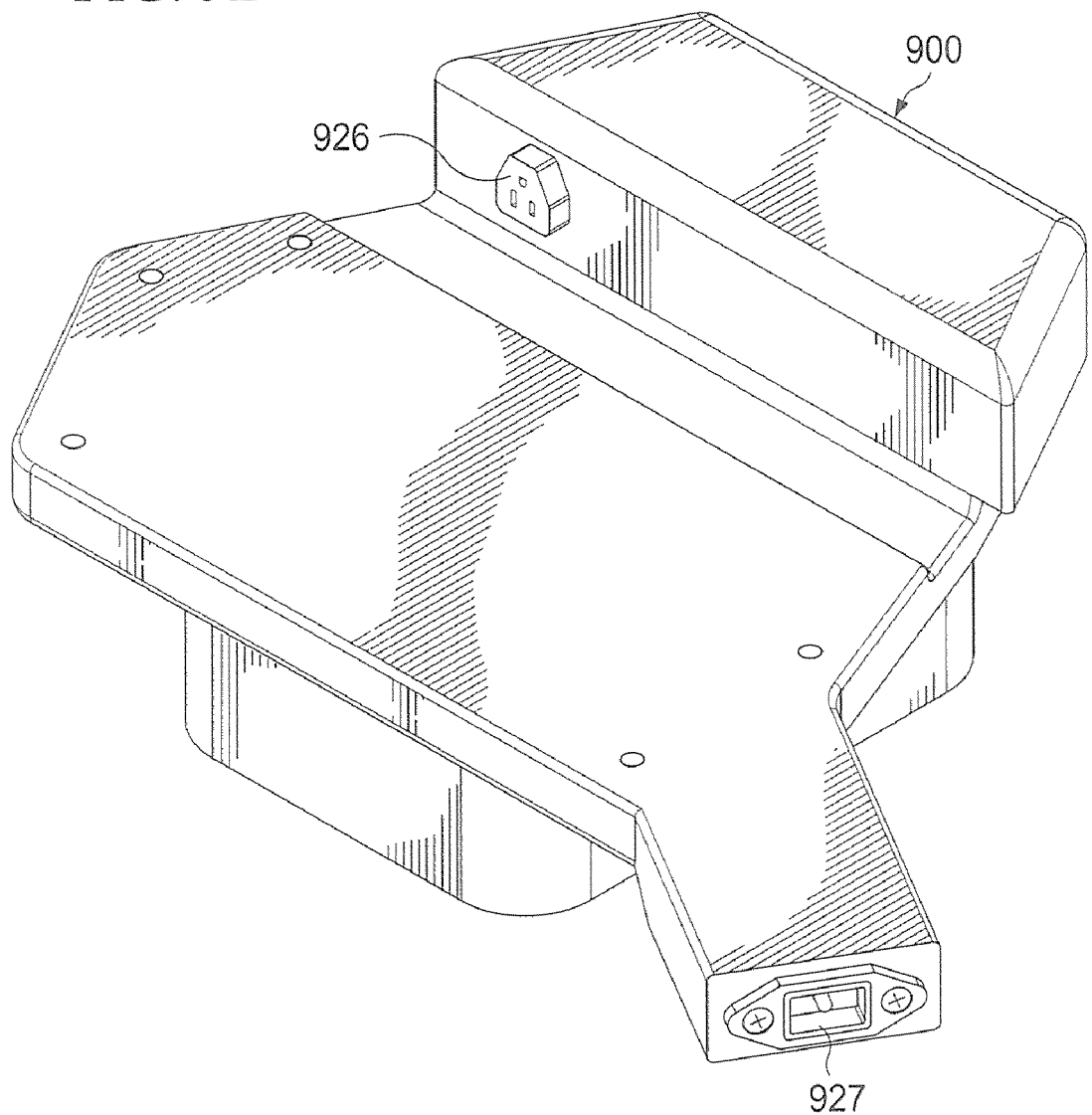

Directing attention to FIG. 7, another embodiment of a docking station system in accordance with the concepts of the present invention is shown as docking station system 700, Docking station system 700 comprises cart 710 provided docking functionality through docking station 800 and docking head 900. As can be seen in the illustrated embodiment, docking head 900 interfaces with docking station 800 to provide connectivity, such as electrical connectivity, data connectivity, etc., between cart 710 and/or devices thereon and one or more devices external thereto, such as premise power, central computer systems, etc. FIG. 8 and FIGS. 9A and 9B, discussed below, provide additional detail with respect to embodiments of docking station 800 and docking head 900.

Referring now to FIG. 8, an embodiment of docking station 800 is shown without corresponding docking head 900 interfaced therewith. Docking station 800 of the illustrated embodiment includes connector 820 for mating with a docking head or other suitably adapted device (e.g., a mobile cart having a corresponding interface). Connector 820 includes one or more conductors 821 to provide electrical connectivity between docking station 800 and a correspondingly mated device. For example, conductors 821 may provide connectivity for premise power delivered to docking station 800 via cord 824 and plug 825. Additionally or alternatively, conductors 821 may provide connectivity for a network interface, data upload, data download, sensors, state detectors, etc. For example, as will be better understood from the discussion of the exemplary docking station wiring diagram below, one or more conductors 821 may provide connectivity for a docking status indicator, such as indicator 826.

Although the illustrated embodiment includes only one connector, it should be appreciated that embodiments may include a plurality of connectors which may be configured the same or differently. For example, a second connector 820, perhaps having a different connector configuration that that of the illustrated embodiment of connector 820, may be provided to make other connections, such as network connections.

Connector 820 of the illustrated embodiment is adapted to facilitate docking cart 710 with docking station 800 wherein electrical and/or other connections are completed without further human intervention. For example, connector 820 of embodiments is disposed in a floating or semi-floating mount allowing at least some movement (e.g., side-to-side, up and down, and/or in and out) of conductors 821 when interfacing with a connector and conductors of a corresponding device (e.g., connector 920 and conductors 921 of docking head 900 shown in FIG. 9A). Such movement may be relatively limited to facilitate desired interfacing of connectors without resulting in large scale movement causing substantial misalignment of the connectors. As an example, sufficient movement of connectors may be provided to allow for small adjustment of connector 820 during docking of docking station 800 and docking head 900 to accommodate slight mismatch of connectors 820 and 920, such as due to manufacturing tolerances, uneven surfaces, etc.

The illustrated embodiment of connector 820 includes guide holes 822 disposed to accept guide pins to facilitate interfacing of the connectors. Directing attention to FIG. 9A, wherein an embodiment of docking head 900 is shown without corresponding docking station 800 interfaced therewith is shown, guide pins 922 disposed about connector 920 in positions corresponding to the positions of guide holes 822 disposed about connector 820 are shown. Guide pins 922 of the illustrated embodiment are of sufficient length to engage guide holes 822 prior to conductors 821 and 921 interfacing. Accordingly, guide pins 922 interfacing with guide holes 822 provides alignment of connectors 920 and 820 to facilitate proper mating of conductors 921 and 821. Embodiments of guide pins 922 and/or guide holes 822 are tapered (e.g., the tips of guide pins 922 and/or the orifice of guide holes 822 present a frustrum of a cone) to accept slight relative displacement between connectors 820 and 920 and provide alignment thereof as the connectors are mated. The aforementioned floating or semi-floating mounting, as may be provided with respect to connector 920 in addition to or in the alternative to connector 820, may be used in combination with the foregoing guide pin and hole configuration to facilitate connector alignment and mating.

The illustrated embodiment of docking station 820 and docking head 920 include adaptations in addition to the foregoing guide holes and pins to facilitate docking and alignment of connectors. For example, docking station 800 includes receiver surfaces 810 which are shaped to guide a corresponding member into a desired docking orientation. Correspondingly, docking head 900 includes boss surfaces 910 to interface with receiver surfaces 810 and guide docking head 920 into a desired docking relationship with docking station 820. These surfaces provide interface surfaces adapted to guide the relative movement between the docking station components such that the desired connections are completed when docked. For example, in the illustrated embodiment, receiver surfaces 810 provide a sufficiently wide point of entry for docking station 800 that docking head 920 need not be precisely positioned to initiate docking. However, as docking head 900 proceeds to dock with docking station 800, receiver surfaces 810 narrow towards the width of the docking head boss portion. Thus, the receiver and boss surfaces cooperate to provide suitable relative movement between the docking station components to align connectors 820 and 920 sufficiently for guide holes 822 and guide pins 922 to engage and provide precise alignment of the conductors.

Because it is expected that receiver surfaces 810 and/or boss surfaces 910 may be exposed to appreciable impact forces during initial docking positioning of cart 710 and friction forces during subsequent docking mating movement, embodiments of the invention adapt one or more such surfaces to withstand such forces. For example, a leading or "nose" area of the boss portion of docking head 900 comprising boss surfaces 910 may be comprised of a nylon, polytetrafluoroethylene (PTFE) or TEFLON, or other suitable material for absorbing impact forces and minimizing frictional forces. For example, a replaceable "wear" item made of one or more such materials may be provided as the boss nose of docking head 900 having boss surfaces 910.

It should be appreciated that guide holes 822 and guide pins 922 provide fine alignment of connectors 820 and 920 while receiving surfaces 810 and boss surfaces 910 provide more coarse alignment of docking station 800 and docking head 900. Embodiments of the invention may include additional adaptation to facilitate docking and alignment of connectors. The illustrated embodiment of docking station 800 includes guide surfaces 811 which may additionally or alternatively be utilized to provide docking alignment. For example, surfaces of cart 710, such as leg surfaces 711 shown in FIG. 7, may interface with guide surfaces 811 to provide alignment of the docking components. Guide surfaces 811 may provide a most coarse, general alignment to encourage an orientation of cart 710 for causing a boss portion of docking head 900 to align with a receiver portion of docking station 800. Thereafter, receiving surfaces 810 and boss surfaces 910 provide less coarse alignment of docking station 800 and docking head 900 to facilitate mating of connectors 820 and 920, whereupon guide holes 822 and guide pins 922 provide fine alignment of connectors 820 and 920 for mating.

Forces applied in docking the components of docking station system 700 may result in forces applied to docking station 800 sufficient to cause its movement, and thus discourage docking, if not adapted to counteract such forces. Accordingly, embodiments of docking station 800 may be rigidly affixed to a premises, such as by fasteners (e.g., screws, nails, bolts, adhesives, etc.) affixing the docking station to a surface such as a floor or wall. Other embodiments of docking station 800 are adapted to discourage undesired movement during docking without such rigid fixation to a premises. For example, embodiments of docking station 800 may comprise bumpers (e.g., bumpers 851 shown in FIG. 7) or other structure to abut a premise wall and prevent movement of docking station 800 away from docking head 900 during docking operations. Additionally or alternatively one or more surface of docking station 800, such as a bottom surface which faces a floor or other support surface, may be adapted to be non-slip, such as through the use of non-slip feet or a non-slip coating (e.g., rubber feet or rubberized surface coating).

Embodiments of docking head 900 are adapted to cooperate with docking station 800 to discourage undesired movement during docking. For example, docking head 900 of the embodiment illustrated in FIG. 9A includes ramp surface 912 which is disposed to interface with a corresponding surface of docking station 800 as the components are docked. As ramp surface 912 slides over the corresponding surface of docking station 800, weight of cart 710 is borne by docking station 800. Thus additional downward pressure, in addition to that due to the weight of docking station 800 alone, is applied to docking station 800. Operation of the aforementioned non-slip feature of docking station 800 may be enhanced by this additional downward force applied during the docking process, thereby discouraging movement of docking station 800 during the docking process.

Docking station 800 and/or docking head 900 may be adapted to hold the docking station components in a docked relationship, and thus facilitate desired transfer of energy, data, etc. through their mated connectors. For example, the illustrated embodiment of docking station 800 includes spring pins 840 disposed to extend through a surface thereof. Correspondingly, docking head 900 includes detents 940 disposed in an opposing surface thereof. During the docking process, while docking head 900 is not in a full mated relationship with docking station 800, spring pins 840 are compressed by the opposing surface of detents 940 so as to be substantially flush with the surface of docking station 800. However, when docking head 900 is fully docked, and in a desired relative position with respect to docking station 800 which provides mating of the connectors thereof, detents 940 are aligned with spring pins 840. Thus spring pins 840 are biased to extend beyond the surface of docking station 800 and engage detents 940. Such biased engagement of spring pins 840 with detents 940 encourages docking station 800 and docking head 900 to remain in the desired relative positions. Surface friction of the opposing surfaces, also providing the aforementioned downward force to docking station 800, may also discourage relative movement between docking station 800 and docking head 900. The spring bias provided by embodiments of spring pins 840 is selected to discourage undesired relative movement between docking station 800 and docking head 900, while permitting desired undocking movement when desired.

Once in a docked relationship, power, data, signals, and/or the like flow through mated connectors 820 and 920. Docking head 900 may provide a plug or other connector to which cart 710 and/or one or more devices of cart 710 are connected. For example, plug 926 (shown in FIG. 9B) is provided in the illustrated embodiment, such as may comprise a standardized plug to which many devices are readily able to connect, to facilitate completing the connection through docking station 800 and docking head 900 to cart 710. For example, on-cart battery system 40 of FIG. 4 may be coupled to plug 926 for providing energy to one or more devices of cart 710. Additionally or alternatively, devices may plug directly into or be wired directly into docking head 900, if desired. Similarly, cart 710 may comprise wiring therein, perhaps providing plugs (not shown) adapted to interface with devices thereon, which may plug directly into or wired directly into docking head 900. Irrespective of the particulars of how connection is made, docking head 900 of embodiments provides connectivity to docking station 800 through connector 920 to cart 710 and/or devices thereof when docked with docking station 800.

Embodiments of docking head 900 facilitate desired connectivity even when not docked with a corresponding docking station. For example, docking head 900 may provide one or more plugs or other connectors for interfacing with premise power, data networks, etc. when separated from docking station 800. Accordingly, cart 710 and/or the devices thereof may be provided energy, signals, services, etc. when being used, such as at a patient's bed or in a surgical theatre, or otherwise deployed.

The illustrated embodiment of docking head 900 includes auxiliary plug 927 (shown in FIGS. 7 and 9B) adapted to provide connectivity to premise power when docking head 900 is not docked with docking station 800. For example, one end of a standard power cord (not shown) may be plugged into auxiliary plug 927 and the other end of the power cord may be plugged into a premise power outlet, such as in a patient's room or other location, to provide line power to devices of cart 710, to recharge batteries of devices of cart 710, etc.

Docking and undocking of docking head 900 provides switched selection between connector 920 and auxiliary plug 927 as the input connector according to embodiments of the invention. For example, to avoid conductors of plug 927 being energized when connector 920 is mated with connector 820 of docking station 800, and similarly to avoid conductors of connector 920 being energized when plug 927 is connected to premise power, embodiments of the invention implement a switched wiring configuration.

Figure 10:
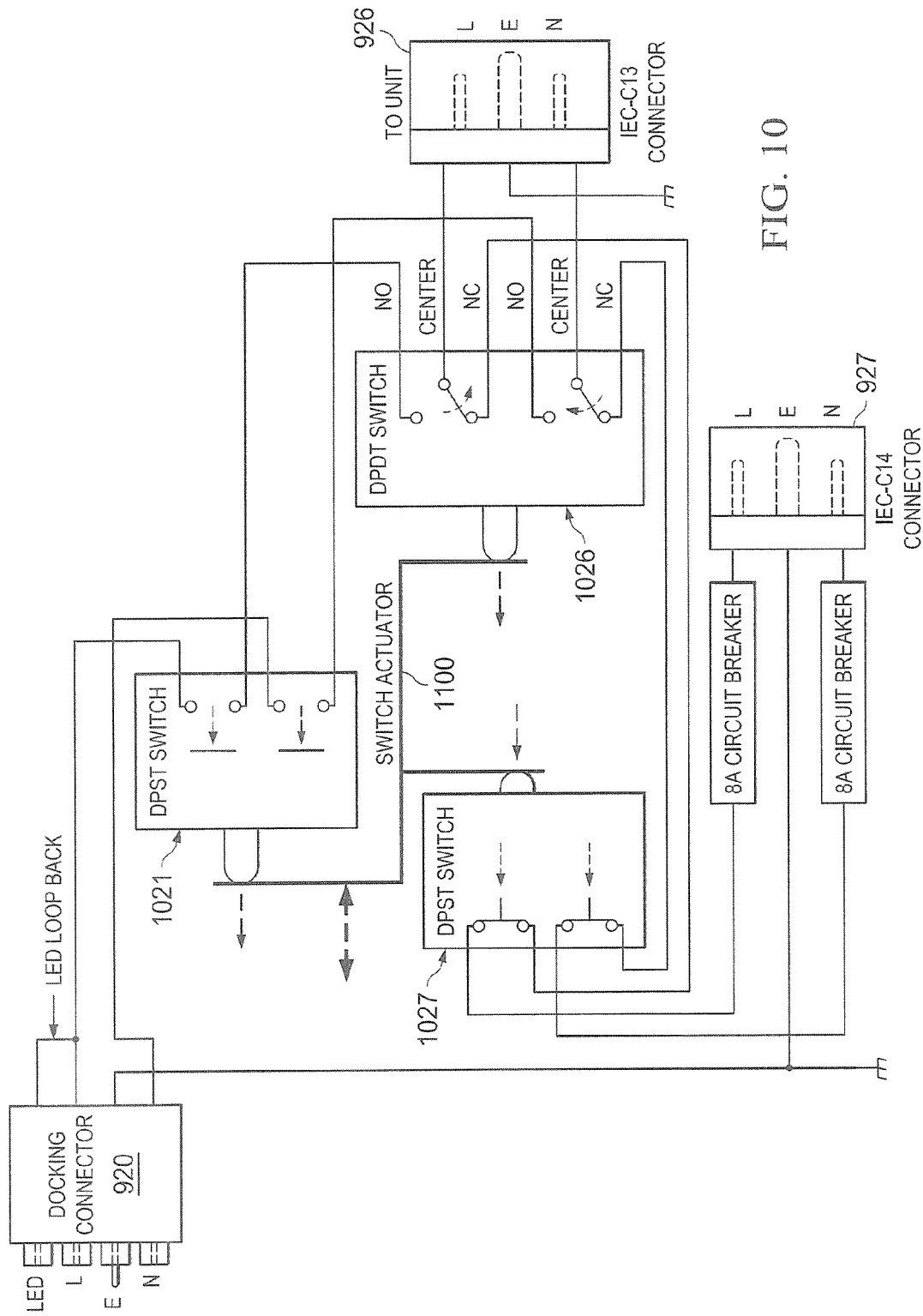
FIG. 10 shows a wiring configuration of a docking head of an embodiment.

Directing attention to FIG. 10, an embodiment of a switched wiring configuration as may be utilized with respect to docking head 900 is shown. In the embodiment illustrated in FIG. 10, double-pole double-throw (DPDT) switch 1026 provides switchable connection of plug 926 for selective connection to either connector 920 or auxiliary plug 927. Accordingly, operation of switch 1026 allows for selectively passing signals between either plug 926 and connector 920 or plug 926 and auxiliary plug 927.

The illustrated embodiment includes double-pole single-throw (DPST) switch 1021 to connect/disconnect connector 920 from the internal wiring of docking head 900 and DPST switch 1027 to connect/disconnect auxiliary plug 927 from internal wiring of docking head 900. Embodiments of docking head 900 include switches 1021 and 1027 in combination with switch 1026 to provide redundancy with respect to isolating an unused plug/connector from energized wiring of docking head 900. Such redundancy may be desirable with respect to particular applications, such as where cart 710 is used in a hospital or similar environment. Embodiments of the invention may, however, utilize fewer switches e.g., utilize only switch 1026) and/or not isolate a plug or connector (e.g., where the plug/connector is disposed to avoid risk of shock due to energized conductors) if desired.

Operation of switched selection of connection of plug 926 either connector 920 or auxiliary plug 927 may be done to provide make-before-break connection or break-before-make connection, as desired. For example, in order to provide optimum safety and isolation of an unused plug/connector from energized wiring of docking head 900 a break-before-make configuration may be utilized. However, in order to provide uninterrupted passage of signals when transitioning between use of one plug/connector and the other plug/connector (e.g., during docking or undocking), embodiments of the invention may utilize a make-before-break configuration.

As with the mating of connectors 820 and 920 being configured to be accomplished through the docking process without further human intervention, switched selection of an appropriate plug/connector of docking head 900 is also configured to be accomplished through the docking process without further human intervention. Accordingly, switch actuator 1100 (FIGS. 10 and 11) is provided according to embodiments to alter switch settings during docking and undocking operations.

Figure 11:
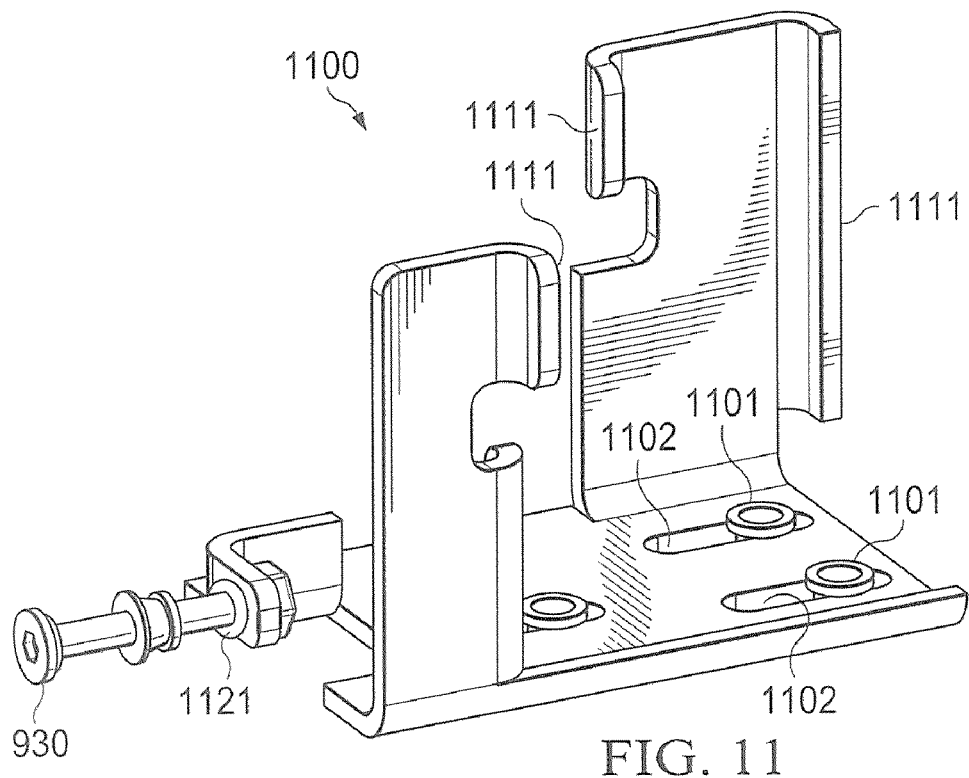
FIG. 11 shows a striker assembly of an embodiment.

Switch actuator 1100 of the embodiment illustrated in FIG. 11 includes striker 930 (also shown in FIG. 9A) which is adapted to interface with a corresponding part of docking station 800 and result in manipulation of switch actuator 1100 during docking/undocking. For example, switch actuator 1100 may be disposed within docking head 900 such that striker 930 is free to move axially (e.g., using tabs 1101 of docking head 900 disposed in slots 1102 of switch actuator 1100) when engaged by corresponding pin 830 of docking station 800. Accordingly, as docking head 900 is docked with docking station 800, pin 830 engages striker 930 which is displaced axially into docking head 900, thereby causing switch actuator to alter the states of switches 1021, 1026, and 1027 of embodiments. Likewise, as docking head 900 is undocked from docking station 800, striker 930 is allowed to move axially in the opposite direction, thereby allowing switch actuator to again alter the states of switches 1021, 1026, and 1027. Tabs (e.g., tabs 1111) or other structure of switch actuator 1100 may interface with switches 1021, 1026, and 1027 to transfer the axial motion of the switching actuator to switch operation motion.

As can be seen in the embodiment of FIG. 11, connectors 820 and 920 of embodiments may carry signals to and from docking head 900. For example, one conductor of connector 920 of the illustrated embodiment is tied to another conductor of connection 920 carrying line voltage to thereby provide a loop back of line voltage when connector 920 is mated with connector 820. This loop back line voltage may be provided to an indicator or sensor, such as power indicator light 826 of FIG. 8, to show that docking has resulted in energizing of docking head 900.

Embodiments of the foregoing docking station system are adapted to provide reliable operation, even when deployed in demanding or harsh environments. For example, in addition to providing rugged housing configurations for docking station 800 and docking head 900, embodiments of the invention adapt moving parts, such as the aforementioned switch actuator, for reliable operation. The embodiment of switch actuator 1100 illustrated in FIG. 11 includes shock mount 1121, such as may comprise a rubber grommet mounting configuration for striker 930, to absorb shocks and undesired loading. For example, side loads (non-axial forces) applied to striker 930 may be accommodated through flexing provided by shock mount 1121. Moreover, forces which may otherwise cause over-travel of striker 930 may be accommodated through compression of shock mount 1121. The embodiment illustrated in FIG. 9A is adapted to dispose striker 930 within a cylindrical housing which, although allows desired axial travel, protects striker 930 from striking or being stricken by objects other than pin 830.

Further, in providing a reliable configuration, embodiments of switch actuator 1100 utilize spring bias forces of one or more switches (e.g., switches 1021, 1026, and/or 1027) to provide axial movement thereof. Such switch spring bias force may be utilized to cause striker 930 to move axially as docking head 900 is undocked from docking station 800. The use of switch spring bias to provide operation of switch actuator 1100 of embodiments leverages otherwise available structure for this purpose without introducing additional, potentially complicated, structure to the configuration, thereby providing a solution which is relatively simple with fewer points of failure.

It should be appreciated that docking head 900 as illustrated in FIGS. 9A and 9B provides a modular configuration which may be attached to cart 710 as an optional feature. Accordingly, cart 710 may be retrofitted with docking head 900 or relieved of docking head 900 as desired. Moreover, docking heads such as docking head 900 may be attached to any number of carts and cart configurations. For example, although embodiments herein have been described with reference to cart 710 having surfaces 711 for facilitating docking with docking station 800, there is no limitation to the use of carts having such a configuration. Accordingly, docking cart 900 may be attached to a cart configuration different than that illustrated in FIG. 7, relying upon aforementioned boss portion and guide pins to orient the cart and docking head for docking.

There is no requirement that a docking head provided in accordance with the concepts of the present invention be modular. Embodiments of the invention comprise a docking head which is integral with a cart or other structure for which docking is to be provided.

Although embodiments have been described herein with reference to ultrasound carts, it should be appreciated that the concepts of the present invention are not limited to applicability with respect to ultrasound devices. Accordingly, docking station systems of the present invention may be utilized with respect to electrocardiogram devices, "crash carts," fetal monitor devices, drug pump devices, etc.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A docking system for a mobile cart, said docking system comprising:

a docking station having a first electrical connector and at least one receiver surface, the docking station adapted for stationary deployment at a premises to provide a docking station location; and a docking head having a second electrical connector and at least one boss surface, the docking head adapted for mobile deployment with the mobile cart, wherein the at least one receiver surface is adapted to interface with the boss surface to guide the docking head into a desired docking orientation with the docking station such that the first electrical connector and second electrical connector mate exclusively through docking movement of the mobile cart relative to the docking station, wherein at least one of the docking station and the docking head include a position locking protuberance and the other one of the docking station and the docking head includes a position locking detent, wherein the position locking protuberance and the position locking detent are disposed to interface when the docking head is disposed in the desired docking orientation and the first electrical connector and second electrical connector are mated to discourage undesired separation of the first electrical connector and the second electrical connector, and wherein the docking head comprises a surface adapted to interface with the position locking protuberance and apply force thereto to work in cooperation with a non-slip structure of the docking station to discourage movement of the docking station during the docking movement of the mobile cart for both docking and undocking.

2. The docking system of claim 1, wherein the position locking protuberance comprises a spring pin.

3. The docking system of claim 1, wherein the docking station comprises a guide surface in addition to the receiver surface, wherein the guide surface is adapted to interface with a surface of the mobile cart to facilitate guiding the docking head into the desired docking orientation.

4. The docking system of claim 3, wherein the guide surface and corresponding mobile cart surface provide coarse positioning of the docking head for docking and the receiver surface and corresponding boss surface provide more fine positioning of the docking head for docking.

5. A docking system for a mobile cart, said docking system comprising:
   a docking station having a first electrical connector and at least one receiver surface, the docking station adapted for stationary deployment at a premises to provide a docking station location; and
   a docking head having a second electrical connector and at least one boss surface, the docking head adapted for mobile deployment with the mobile cart,
      wherein the at least one receiver surface is adapted to interface with the boss surface to guide the docking head into a desired docking orientation with the docking station such that the first electrical connector and second electrical connector mate exclusively through docking movement of the mobile cart relative to the docking station,
      wherein the docking head includes an auxiliary electrical connector configured to carry signals otherwise carried by the second electrical connector when the docking head is docked with the docking station, and
      wherein the docking head comprises a switch and switch actuator assembly adapted to selectively connect either the second electrical connector to circuitry of the mobile cart or the auxiliary electrical connector to circuitry of the mobile cart.

6. The docking system of claim 5, wherein the switch actuator is configured to change a state of the switch exclusively through the docking movement of the mobile cart relative to the docking station.

7. The docking system of claim 5, wherein the mating of the first electrical connector and the second electrical connector provide premise power to the mobile cart.

8. The docking system of claim 5, wherein the docking head comprises a removable module attached to the mobile cart.

9. A method for providing premise power to a mobile cart, the method comprising:
   providing a docking station having a first electrical connector, at least one receiver surface, and at least one non-slip surface;
   providing a docking head having a second electrical connector, at least one boss surface, and at least one ramp surface, wherein the docking head is adapted to be affixed to the mobile cart for use in docking with the docking station;
   configuring the receiver surface and the boss surface to cooperatively guide the docking head into a desired docking orientation with the docking station such that the first electrical connector and the second electrical connector mate through a docking movement of the mobile cart relative to the docking station;
   configuring the ramp surface to engage a corresponding top surface of the docking station and apply force thereto to work in cooperation with the non-slip surface to discourage movement of the docking station during the docking movement of the mobile cart for both docking and undocking; and
   providing an actuatable switch circuit, wherein the switch circuit is configured to be actuated by the docking movement to select between an auxiliary electrical connector and the second electrical connector for coupling to devices of the mobile cart.

10. The method of claim 9, wherein the docking station further has a guide surface and the mobile cart has a corresponding surface, the method further comprising:
    configuring the guide surface to interface with the corresponding surface of the mobile cart to facilitate guiding the docking head into the desired docking orientation.

11. The method of claim 9, wherein at least one of the ramp surface and the corresponding top surface of the docking station include a position locking protuberance and the other one of the ramp surface and the corresponding top surface of the docking station includes a position locking detent, and further comprising:
    configuring the position locking protuberance and the position locking detent to interface when the docking head is disposed in the desired docking orientation and the first electrical connector and second electrical connector are mated to discourage undesired separation of the first electrical connector and the second electrical connector.

12. A system comprising:
    a mobile cart configured to provide mobile support for at least one medical device;
    a docking head attached to the mobile cart and configured to be electrically coupled to the at least one medical device, the docking head having a docking head connector disposed on a docking head boss, the docking head boss adapted to guide the docking head into a docked orientation whereby the docking head connector is mated with a corresponding connector; and
    a docking station having a docking station connector and one or more receiver surfaces, wherein the receiver surfaces are configured to receive the docking head boss to guide the docking head into the docked orientation whereby the docking head connector is mated with the docking station connector when the mobile cart is moved in proximity to the docking station,
       wherein the mated docking head connector and docking station connector are adapted to provide premise power to the at least one medical device,
       wherein the docking head further has an auxiliary plug adapted to provide the premise power to the at least one medical device when the docking head is not disposed in the docked orientation; and
       wherein the docking head further has a switching circuit to selectably connect either the docking head connector or the auxiliary plug to the at least one medical device, the switching circuit including a switch actuator which is operable in response to the docking head docking with the docking station.

* * * * *